(12) United States Patent
Wojcik et al.

(10) Patent No.: US 7,429,737 B2
(45) Date of Patent: Sep. 30, 2008

(54) RETROFIT DIGITAL MAMMOGRAPHY DETECTOR

(75) Inventors: Timothy J. Wojcik, Rochester, NY (US); Jeffrey W. Byng, Toronto (CA); Bradley S. Jadrich, Rochester, NY (US); Mark E. Shafer, Fairport, NY (US); Kwok-Leung Yip, Webster, NY (US)

(73) Assignee: Carestream Health, Inc., Rochester, NY (US)

( * ) Notice: Subject to any disclaimer, the term of this patent is extended or adjusted under 35 U.S.C. 154(b) by 0 days.

(21) Appl. No.: 11/558,128

(22) Filed: Nov. 9, 2006

(65) Prior Publication Data

US 2008/0112535 A1   May 15, 2008

(51) Int. Cl.
*G01T 1/24* (2006.01)
(52) U.S. Cl. .................................. 250/370.09
(58) Field of Classification Search ................. 250/367, 250/370.09, 370.14, 484.4; 378/98.8
See application file for complete search history.

(56) References Cited

U.S. PATENT DOCUMENTS

| | | | | |
|---|---|---|---|---|
| 4,179,100 A | * | 12/1979 | Sashin et al. | ........... 250/370.09 |
| 5,319,206 A | | 6/1994 | Lee et al. | |
| 5,331,166 A | * | 7/1994 | Yamamoto et al. | ..... 250/370.11 |
| 5,528,043 A | * | 6/1996 | Spivey et al. | .......... 250/370.09 |
| 5,650,626 A | | 7/1997 | Trauernicht et al. | |
| 5,661,309 A | * | 8/1997 | Jeromin et al. | .............. 250/580 |
| 5,715,292 A | | 2/1998 | Sayag et al. | |
| 5,844,961 A | * | 12/1998 | McEvoy et al. | ............ 378/98.8 |
| 6,592,257 B1 | | 7/2003 | Heidsieck et al. | |
| 6,734,441 B2 | | 5/2004 | Wendlandt | |
| 6,800,870 B2 | | 10/2004 | Sayag | |

OTHER PUBLICATIONS

International Standard ISO 4090:2001(E) "Photography-Medical radiographic cassettes/screens/films and hard-copy imaging films-Dimensions and specifications".

* cited by examiner

*Primary Examiner*—David P. Porta
*Assistant Examiner*—Mark R Gaworecki

(57) ABSTRACT

A digital radiography (20) detector has a first housing (18) having substantially the form factor of a film cassette and having a chest wall edge (C). The first housing (18) has an X-ray converter (70) with a detection array (26), each detector generating a signal according to an amount of radiation received. Readout electronics (74) are coupled with switching elements in the detection array for obtaining the signals therefrom. The readout electronics (74) include elements formed from crystalline silicon and are distributed toward outer edges of the first housing (18) and away from the chest wall edge (C). X-ray shielding selectively protects the readout electronics (74) and is located beneath a portion of the detection array. A second housing (40), electrically connected to the first housing (18) has a power source for the detector, readout and control electronics for obtaining signals provided from the detection array (26).

20 Claims, 12 Drawing Sheets

| SUBSTRATE | SUBSTRATE THICKNESS (mm) | X-RAY ABSORPTION EFFICIENCY OF SUBSTRATE FOR MAMMO BEAM* (%) | FOR DR DETECTOR 1 | | FOR DR DETECTOR 2 | | FOR DR DETECTOR 3 | |
|---|---|---|---|---|---|---|---|---|
| | | | X-RAY TRANSMISSION THROUGH CASSETTE PANELS, A 84-μm Gd2O2S SCREEN AND SUBSTRATE FOR MAMMO BEAM* (%) | X-RAY EXPOSURE AT AEC SENSOR+ FOR A 84-μm Gd2O2S SCREEN (mR) | X-RAY TRANSMISSION THROUGH CASSETTE PANELS, A 150-μm CsI SCREEN, AND SUBSTRATE FOR MAMMO BEAM* (%) | X-RAY EXPOSURE AT AEC SENSOR+ FOR A 150-μm CsI SCREEN (mR) | X-RAY TRANSMISSION THROUGH CASSETTE PANELS, A 75-μm a-Se LAYER, AND SUBSTRATE FOR MAMMO BEAM* (%) | X-RAY EXPOSURE AT AEC SENSOR+ FOR A 75-μm a-Se LAYER (mR) |
| CORNING 1737 GLASS | 0.7 | 62.02 | 8.74 | 1.05 | 5.28 | 0.63 | 5.64 | 0.68 |
| | 0.4 | 43.41 | 13.02 | 1.56 | 7.87 | 0.94 | 8.41 | 1.01 |
| CORNING EAGLE 2000 GLASS | 0.7 | 41.02 | 13.57 | 1.63 | 8.21 | 0.98 | 8.76 | 1.05 |
| | 0.635 | 38.16 | 14.23 | 1.71 | 8.60 | 1.03 | 9.19 | 1.10 |
| | 0.6 | 36.55 | 14.60 | 1.75 | 8.83 | 1.06 | 9.43 | 1.13 |
| | 0.5 | 31.69 | 15.72 | 1.89 | 9.50 | 1.14 | 10.15 | 1.22 |
| STAINLESS STEEL FOIL (302) | 0.406 | 99.6 | 0.09 | 0.01 | 0.05 | 0.01 | 0.06 | 0.01 |
| | 0.203 | 96.5 | 0.81 | 0.10 | 0.49 | 0.06 | 0.53 | 0.06 |
| | 0.178 | 95.1 | 1.13 | 0.14 | 0.68 | 0.08 | 0.73 | 0.09 |
| | 0.127 | 89.9 | 2.32 | 0.28 | 1.40 | 0.17 | 1.50 | 0.18 |
| | 0.102 | 85.1 | 3.42 | 0.41 | 2.07 | 0.25 | 2.21 | 0.26 |
| | 0.076 | 77.1 | 5.28 | 0.63 | 3.19 | 0.38 | 3.41 | 0.41 |
| | 0.051 | 64.1 | 8.26 | 0.99 | 4.99 | 0.60 | 5.33 | 0.64 |
| | 0.025 | 41.1 | 13.55 | 1.63 | 8.19 | 0.98 | 8.75 | 1.05 |
| ANODIZED ALUMINUM FOIL | 0.381 | 33.29 | 15.35 | 1.84 | 9.28 | 1.11 | 9.91 | 1.19 |
| | 0.254 | 23.85 | 17.53 | 2.10 | 10.59 | 1.27 | 11.31 | 1.36 |
| | 0.178 | 17.48 | 18.99 | 2.28 | 11.48 | 1.38 | 12.26 | 1.47 |
| | 0.127 | 12.85 | 20.06 | 2.41 | 12.12 | 1.45 | 12.95 | 1.55 |
| | 0.102 | 10.48 | 20.60 | 2.47 | 12.45 | 1.49 | 13.30 | 1.60 |
| POLYETHYLENE TEREPHTHALATE (PET) | 1.1 | 9.05 | 20.93 | 2.51 | 12.65 | 1.52 | 13.51 | 1.62 |
| | 0.7 | 5.86 | 21.67 | 2.60 | 13.10 | 1.57 | 13.99 | 1.68 |
| | 0.4 | 3.40 | 22.23 | 2.67 | 13.44 | 1.61 | 14.35 | 1.72 |
| | 0.178 | 1.53 | 22.66 | 2.72 | 13.70 | 1.64 | 14.63 | 1.76 |
| | 0.102 | 0.88 | 22.81 | 2.74 | 13.79 | 1.65 | 14.73 | 1.77 |

*MAMMO BEAM: 28kVp, Mo tube, 1mm Be & 0.03mm Mo & 4.5cm LUCITE & 1m AIR, Q=100000 PHOTONS/mm2, X=1.99mR, Q/X=50100 phot/mm2-mR, HVL=0.636mm Al
+INCLUDING TRANSMISSION LOSSES THROUGH THE CASSETTE FRONT/BACK PANELS, SCREEN, AND SUBSTRATE; INCIDENT EXPOSURE AT THE CASSETTE FRONT IS 12 mR
NOTE: ISO CASSETTE STANDARD - REQUIRED MINIMUM EXPOSURE AT AEC SENSOR ~ 5 uGy TO 10 uGy (0.57 mR TO 1.14 mR)

*FIG. 11*

RETROFIT DIGITAL MAMMOGRAPHY DETECTOR

CROSS REFERENCE TO RELATED APPLICATIONS

Reference is made to commonly-assigned copending U.S. patent application Ser. No. 11/441,584, filed May 26, 2006, entitled COMPACT AND DURABLE ENCASEMENT FOR A DIGITAL RADIOGRAPHY DETECTOR, by Jadrich et al., and to U.S. patent application Ser. No. 11/409,883, filed Apr. 24, 2006, entitled WIRELESS X-RAY DETECTOR FOR A DIGITAL RADIOGRAPHY SYSTEM WITH REMOTE EVENT DETECTION, by Dhurjaty et al., the disclosures of which are incorporated herein.

FIELD OF THE INVENTION

This invention relates in general to medical imaging systems that use digital radiography detectors, and more particularly to a digital radiography detector that can be retrofit into an existing film-based mammography exposure system.

BACKGROUND OF THE INVENTION

Traditional film-screen radiography has been used as a medical imaging diagnostic system for many years. X-rays are projected through a patient's body part to irradiate a cassette containing a scintillator screen that converts the X-rays to light to form a latent radiographic image on a sheet of film placed in direct contact with the screen. The film is then chemically or thermally processed to produce a visual radiographic image that can be used by a health care professional for diagnostic purposes. Problems with conventional film based systems include delay in obtaining a diagnostic image, the requirement for chemical or thermal processing, and difficulty in providing the radiographic image outside of the immediate medical facility. These and other problems with film-based solutions have motivated the development of digital radiographic imaging systems.

One aspect of conducting radiographic imaging is the importance of controlling the amount of X-ray exposure that the patient and the detector receive since excessive exposure to this ionizing radiation can be harmful to the patient and would create undesirable density levels on film. Automatic exposure control (AEC) apparatus have been developed with this purpose in mind and are available with a broad range of film-based systems, including mammography systems. Automatic exposure controls (AECs) monitor exposure with detectors placed in the radiation path and sense this radiation level to automatically terminate the X-ray emission at the appropriate time. The AEC detector is typically placed in front of the imaging cassette when using higher energies as are typically used in general radiography. In the case of mammography, in which lower X-ray energy levels are used to improve subject contrast, the AEC detector is preferably placed behind the imaging cassette, in order to reduce the possibility of creating undesirable interference with the radiographic image caused by absorption of the X-rays by the AEC detector.

Recently, computed radiography (CR) digital systems have been developed for mammography that utilize reusable storage phosphor plates that are scanned to produce a digital radiographic image. The storage phosphor plate is typically contained in a cassette that can be the same size as film cassettes and the screen/cassette combination has radiographic attenuation properties that make it compatible with existing X-ray exposure and AEC systems. CR systems have been well received in the market since they provide many of the benefits of digital imaging while utilizing existing X-ray exposure systems thus minimizing the cost of converting to digital imaging. However, among other problems, the CR systems still result in a delay in obtaining a diagnostic image due to the necessity of removing the CR cassette from its position within the imaging apparatus and scanning the exposed CR plate.

Digital radiographic mammography is achieving growing acceptance as an alternative to film-screen and CR radiography systems. With digital radiography (DR), the radiation image exposures that have been captured on radiation sensitive layers are converted, pixel-by-pixel, to digital image data that is stored and subsequently displayed on electronic display devices. One of the driving forces in the success of digital radiography is the ability to rapidly visualize and communicate a radiographic image via networks to a remote location for analysis and diagnosis by radiologists, without chemical or thermal processing cost and delay and without delays in transmittal of hard copy processed radiographic films by courier or through the mail. Further, increased detective quantum efficiency (DQE) of DR detectors enables improved image quality at lower patient radiation dosage.

DR detectors can either be direct or indirect conversion devices. Direct detectors use a material such as selenium in contact with a TFT array for conversion of X-ray photons to electronic charge signals that are subsequently converted to a digital representation of the image. Indirect detectors use a scintillator screen for conversion of X-rays to visible light that is then detected via contact with an amorphous silicon photodiode and TFT array. Both types of DR detector have been shown to produce diagnostic quality images.

Today's solid-state, ionizing radiation-based image detectors (hereafter DR detector) used in projection digital radiography are relatively large and expensive. These detectors typically include the following major components: a protective housing; the X-ray converter material; a glass substrate with amorphous silicon circuitry that captures and selectively provides image signals on a pixel basis; high density interconnect circuits to receive readout commands and to transfer the image signals to conversion electronics; readout ASICs to amplify the signal charge and multiplex the signals for analog-to-digital conversion; and additional electronics to control the panel operation and transfer the digital image data to a host computer. There are a number of design constraints with these devices. For example, the low signal levels in these systems require that the physical distance from the detection panel to the readout electronics remain as short as possible to achieve acceptable signal-to-noise ratios, thus driving the detector assembly to contain a significant portion of its electronics components within the detector assembly enclosure. Many of the electronic components themselves require protection from the imaging X-rays, typically in the form of lead shielding, to reduce the risk of damage or malfunction.

Cost remains a significant problem. Complete mammography DR systems using this type of detector require substantial capital investment, as the system typically includes proprietary hardware such as the DR detector, operator interface, processing computer, X-ray generator, X-ray source, and patient positioner. As a result, DR systems are very expensive and the current market is small given the high cost of investment. Present DR detector based systems are not compatible with film-based systems, thus do not provide a digital imaging solution for the large installed base of X-ray imaging systems that presently support film or CR cassettes. It is therefore desirable to provide a DR detector based imaging system that is backward compatible with the large installed base of mammography X-ray imaging systems.

In an effort to ensure compatibility with X-ray exposure equipment, the dimensions of medical radiographic cassettes/ screens/films are specified under International Standard ISO 4090:2001(E), entitled "Photography—Medical Radiographic cassettes/screens/films and hard-copy imaging films—Dimensions and specifications." This specification encompasses both conventional film and CR phosphor screens, with nominal imaging areas up to 18 cm×24 cm and 24 cm×30 cm (metric origin) for mammography. Standard cassette dimensions are specified as part of this ISO standard, including the maximum cassette thickness of roughly 16.0 mm. The "free field for radiation detector" section of this standard specifies the area and X-ray transmission characteristics of the cassette/screen/film to ensure compatibility with conventional AEC systems.

There have been numerous types of X-ray equipment and configurations designed and used for specific radiographic procedures. For example, these systems include wall-stand, floor-mount, chest, or table units; designed for supine, upright, or other patient orientations. Particular systems have been designed to enable efficient operation of mammographic screening procedures. Major manufacturers of traditional X-ray equipment include, for example, Siemens, Philips, and General Electric. It has been estimated that worldwide installations of traditional mammography X-ray equipment exceed over 30,000 units. In order to serve owners and users of this sizable installation base and to provide them with the advantages of DR imaging technology, it would be advantageous to provide a retrofit DR detector that allows a relatively seamless transition from film-based imaging to digital imaging.

With this general goal in mind, there have been a number of proposed solutions to the problem of adapting DR imaging solutions to existing film-based X-ray systems, including the following:

U.S. Pat. No. 5,844,961 (McEvoy et al.), discloses a filmless digital X-ray system that is designed to be compatible with standard X-ray cassette housing external dimensions, but does not provide compatibility with existing mammography AEC systems.

U.S. Pat. No. 6,592,257 (Heidsieck et al.), and U.S. Pat. No. 5,715,292 (Sayag et al.), disclose small area mammography spot imaging detectors that are used for diagnostic procedures such as needle biopsies and are compatible with film cassette holders but do not provide full field imaging capability or compatibility with AEC systems.

U.S. Pat. No. 6,800,870 (Sayag), discloses a CR screen and reading system that is compatible with film cassette based X-ray exposure systems but requires readout of a storage phosphor plate after exposure, thus delaying image availability.

U.S. Pat. No. 6,734,441 (Wendlandt), discloses features of a CR cassette design that is compatible with AEC systems but still requires readout of a storage phosphor plate after exposure, thus delaying image availability.

As solutions such as these show, the need for digital retrofit to film-based systems has been well recognized. However, proposed solutions for DR retrofit apparatus have not addressed the particularly challenging requirements of full-field mammography imaging. A digital retrofit device must fit within the existing form factor of a mammography film cassette, requiring compact packaging. At the same time, AEC compatibility is an important requirement for compatibility with existing radiology systems, and provides even further constraints on component packaging. Providing the required chest wall access distance is yet a further challenge. Thus, it can be appreciated that there is a need for a retrofit digital mammography detector that offers DR advantages and that is compatible with existing X-ray equipment.

SUMMARY OF THE INVENTION

The present invention is directed to providing a system that addresses the problems and the needs discussed above. The present invention provides a digital radiography detector comprising:
   a) a first housing, having substantially the form factor of a film cassette and having a chest wall edge, the first housing comprising:
      (i) an X-ray converter coupled with a detection array, wherein each detector in the detection array generates a signal according to an amount of radiation received by the X-ray converter;
      (ii) readout electronics coupled with switching elements in the detection array for obtaining the signals therefrom, wherein the readout electronics comprise elements formed from crystalline silicon and wherein the readout electronics are distributed toward outer edges of the first housing and away from the chest wall edge of the first housing;
      (iii) X-ray shielding protecting the readout electronics and located beneath a portion of the X-ray converter; and
   b) a second housing electrically connected to the first housing and comprising:
      (i) a power source for the detection and switching element arrays; and
      (ii) control electronics for obtaining signals provided from the readout electronics in the first housing.

It is a feature of the present invention that it provides a DR detector having a predefined area that is substantially transmissive to X-ray radiation.

It is an advantage of the present invention that it provides a digital radiography retrofit device that uses existing automatic exposure control systems.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 11 is a table showing X-ray transmission characteristics for various substrates and scintillating phosphor types.

DETAILED DESCRIPTION OF THE INVENTION

Figure 1:
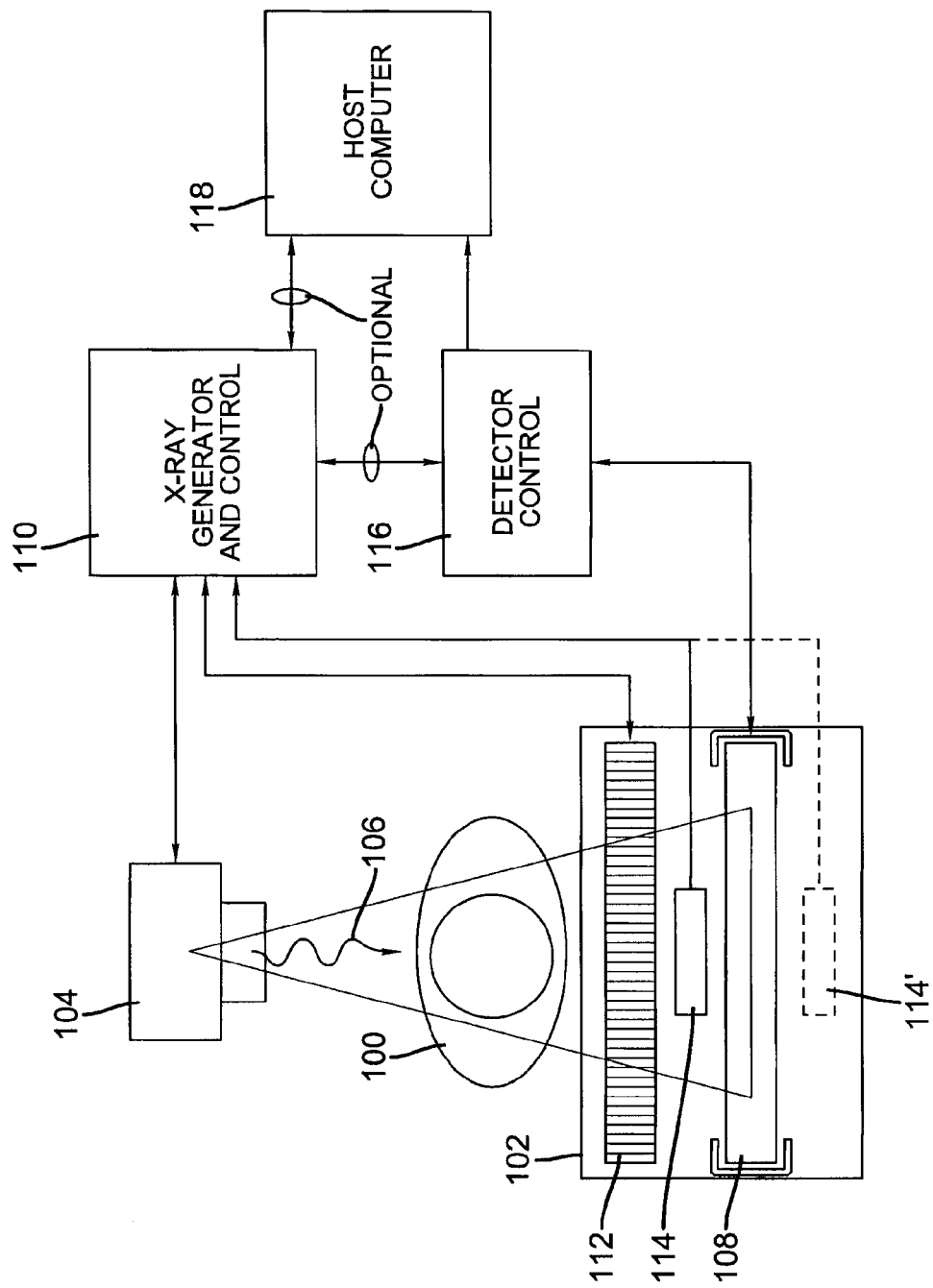
FIG. 1 is a diagrammatic view of typical X-ray equipment in today's X-ray examination room.

The following is a detailed description of the preferred embodiments of the invention, reference being made to the drawings in which the same reference numerals identify the same elements of structure in each of the several figures.

Referring now to FIG. 1, there is shown a typical projection X-ray apparatus used in an X-ray examination room. As shown, a patient 100 is positioned on a support 102. An X-ray source 104 projects X-rays 106 through a body part of patient 100 to form a radiographic image of the corresponding anatomy, which is detected by a digital detector housed in a radiography cassette 108 mounted in support 102. X-ray source 104 is activated and controlled by an X-ray generator and control 110. Support (Bucky) 102 can also house an antiscatter grid 112. An auto exposure control (AEC) sensor 114 can be positioned in the path of X-rays 106, prior to radiography cassette 108. Alternately, as is generally practiced for mammography, an auto exposure control (AEC) sensor 114' is disposed below radiography cassette 108. A detector control 116 is linked to digital detector in radiography cassette 108 and to a host computer 118. Antiscatter grid 112 and auto exposure controls 114, 114' are linked to X-ray generator and control 110 which is typically linked to an external computer or other control logic processor.

Figure 2:
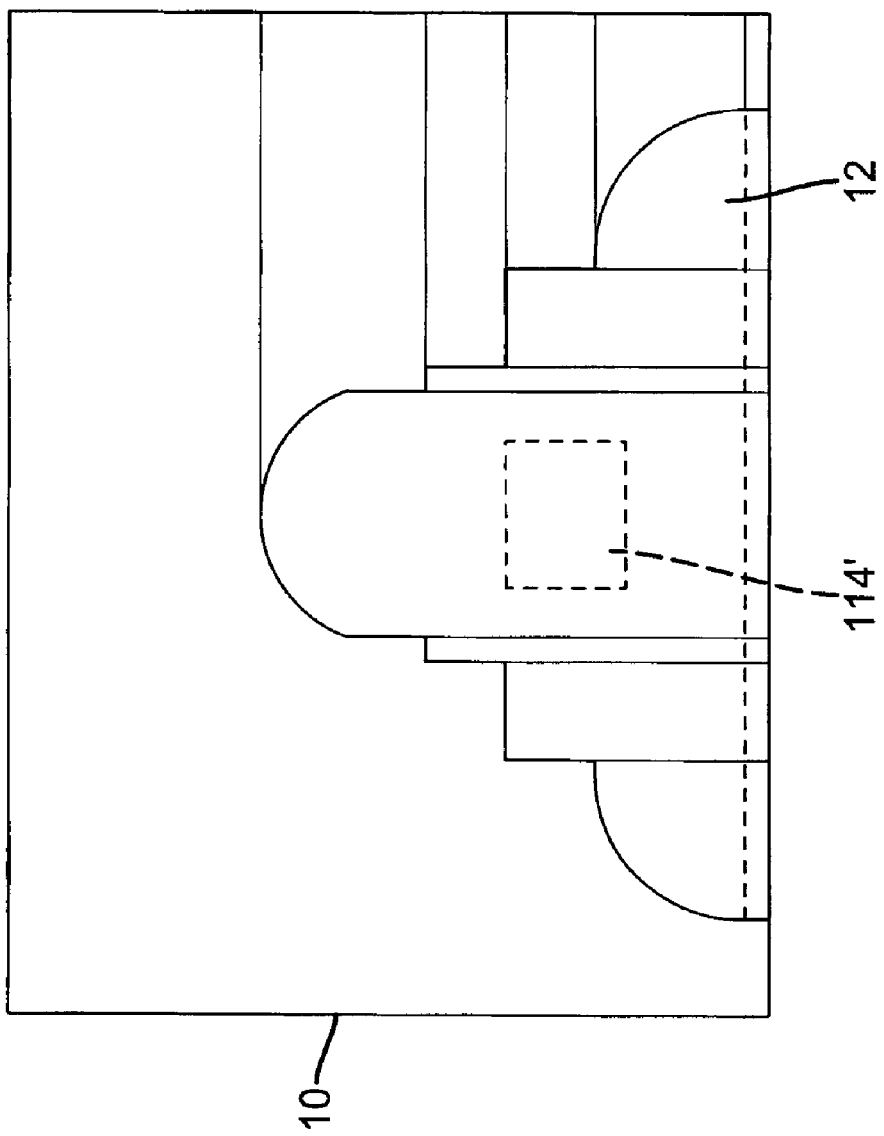
FIG. 2 is a plan view showing the free-field area required for automatic exposure control.

The ISO 4090:2001 standard cited earlier stipulates specific dimensional requirements for free-field access needed by AEC devices. Referring to FIG. 2, there is shown a plan view of the free-field requirement for a radiation detector 10 used in mammography according to this standard. A free-field area 12 is defined as an area within which detector 10 should provide a minimum of attenuation. The relative position of auto exposure control sensor 114' is represented in dotted outline in FIG. 2; in practice, sensor 114' can be positioned anywhere within free-field area 12 when considered from this view. Minimum attenuation over this area allows AEC controls to work over their optimal sensitivity range, helping to minimize exposure risks to the patient and to present a desirable exposure level to the imaging detector.

Yet another challenge to detector packaging relates to chest wall access, referred to in terms of film-thorax distance in the ISO 4090:2001 specification. It is important that no more than a minimum access distance be allowed from the edge of the detector assembly to its active area, in order to maximize the imageable area. This places further constraints on detector design, requiring compact packaging while restricting component dimensions and placement.

In conventional DR detector design, a number of support electronics components require shielding from incident radiation. Still other electronic components for providing power and logic signals, while not requiring radiation shielding, present obstacles to radiation that would tend to attenuate the signal and thus degrade AEC sensor 114' performance. The substrate material, on which the DR detection array is deposited, similarly presents an obstacle to radiation that tends to attenuate the signal and degrade AEC sensor 114' performance. Thus, it can be appreciated that conventional approaches to DR detector design are poorly suited to the task of retrofit DR detector design for mammography imaging.

In order to provide a retrofit DR detector for these systems, the present invention takes a novel approach to component packaging unlike that conventionally followed in DR detector design. The apparatus and method of the present invention can utilize either of the two key types of DR detection apparatus: the indirect DR apparatus, as shown in the schematic block diagram of FIG. 3A or the direct DR apparatus, shown in the schematic block diagram of FIG. 3B. These two types of imaging apparatus differ primarily in how the original image signal is generated in a detector assembly 20 that uses an X-ray converter 70, provided in a cassette housing 18. In both types of detector, X-ray converter 70 is coupled with a detection array 26 that is appropriately configured for the mode of signal generation.

Indirect DR systems use an intensifying phosphor screen (scintillator) 22 to convert X-ray radiation into visible light. A detailed explanation of this conversion process and detection system is disclosed in U.S. Pat. No. 5,650,626, (Trauernicht et al.). As is well known to those skilled in the imaging arts, pixellated elements in a detection array 26 are electronically coupled with corresponding row/column driver electronics that synchronously switch signals from detection array 26 to downstream imaging circuits that perform image collection and formation. In the indirect DR device of FIG. 3A, a scintillator screen 22 provides light output in response to received radiation. A detection module 24 includes detection array 26, wherein each detector in the array generates a signal corresponding to a received level of light from scintillator screen 22, in a pixel arrangement familiar to those skilled in the imaging arts. The light sensors and supporting signal switching circuitry used to provide each pixel element in detection array 26 are thin-film components that present characteristically low attenuation to incident X-rays.

Direct DR systems use a layer of photoconductor material such as amorphous selenium (a-Se) or lead iodide ($PbI_2$) to convert X-ray radiation to electrical charge. A detailed explanation of this conversion process and detection system is disclosed in U.S. Pat. No. 5,319,206 (Lee et al.). In the direct DR apparatus of FIG. 3B, cassette housing 18 has a detection array 26 that is electrically coupled with a photoconductor layer. Each pixel of the detection array incorporates a conductive electrode to collect the charge and a capacitor element to store it. Each element in the array provides an output signal proportional to received X-ray radiation and is coupled with a switching element that gates the output signal to a signal line, as is familiar to those skilled in the imaging arts. The detection process is direct in that the image information is transferred from X rays directly to electrical charge with no intermediate stage.

For both indirect DR (FIG. 3A) and direct DR (FIG. 3B) embodiments, readout electronics 74 are then used to obtain the signal generated from each pixel element, in row and column fashion, in order to provide the two-dimensional image data. Unlike the pixel signal switching elements that are provided as part of detection array 26, readout electronics 74 are conventional integrated circuit components. Formed from crystalline silicon and thus exhibiting sensitivity to damage from incident X-rays, readout electronics 74 include the components for column readout circuitry 28, row control circuitry 30, and readout control circuitry 32. These components are typically shielded from X-ray radiation, as described subsequently. An electronics housing 40 contains a power supply 42 and sequencing control 44 components, used for data formatting and interface functions. An external computer 50 includes a control logic processor 52, a high-speed interface 54, and an image handling subsystem 56, as well as display and other components.

Figure 3A:
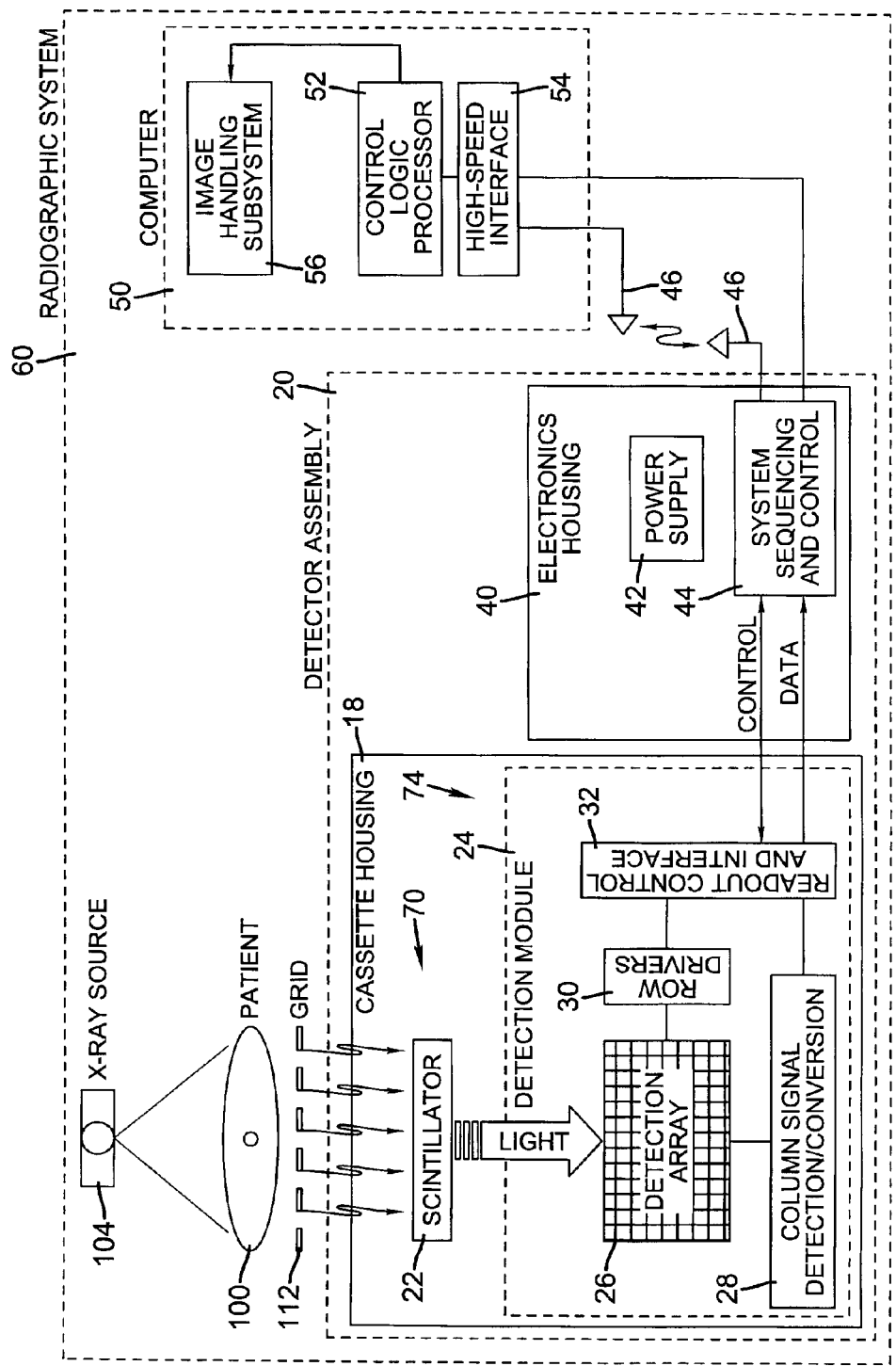
FIG. 3A is a block diagram showing components of a detector assembly using a scintillator screen in relation to other imaging system components.
Figure 3B:
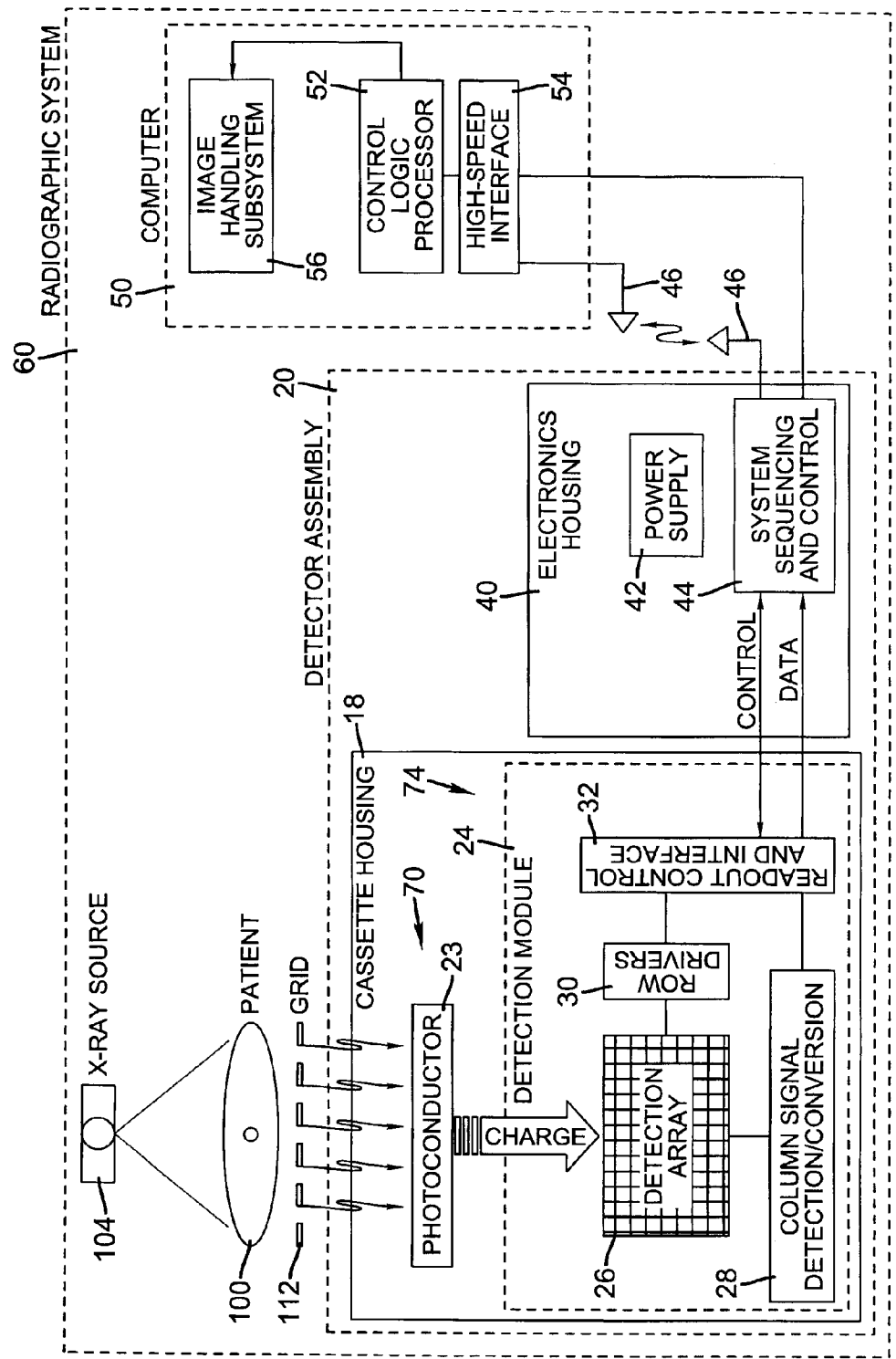
FIG. 3B is a block diagram showing components of a detector assembly using direct detection of radiation in relation to other imaging system components.
Figure 4:
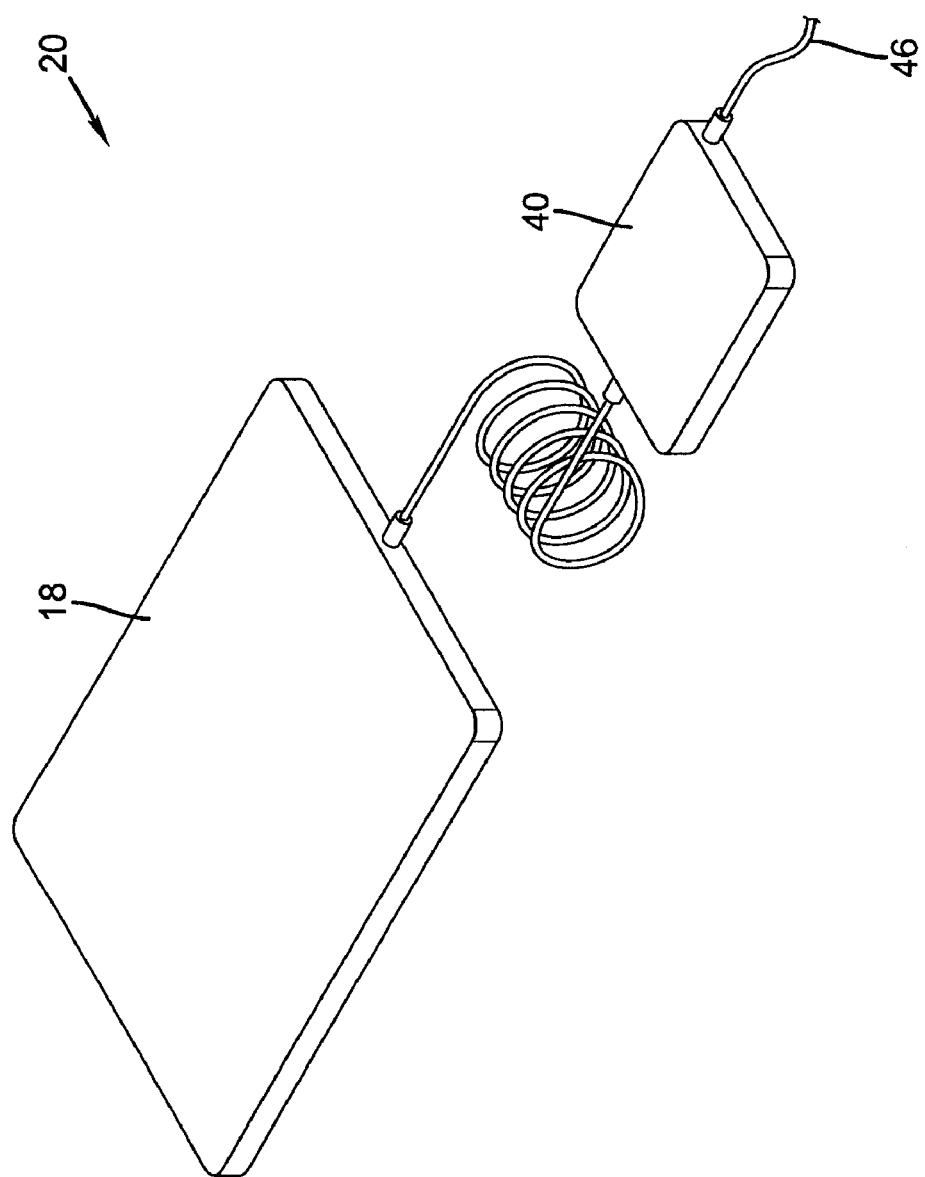
FIG. 4 is a perspective view of a detector in one embodiment using a tethered electronics assembly.

The perspective view of FIG. 4 shows one arrangement of detector 20 components that uses a tethered arrangement. With this configuration, housing 18 contains the components that are necessary for obtaining the image signals, as shown in FIGS. 3A and 3B. Electronics housing 40 connects to housing 18 components with a wired connection, allowing power supply and some portion of the electronics components to be positioned a short distance away from the imaging area. This arrangement allows housing 18 to have the form factor of a mammography film cassette, in one embodiment. An optional antenna 46 or other type of wireless transmission mechanism may serve to provide the interface with external computer 50. This could also be a hard-wired connection for data transmission.

Advantageously, with the arrangement shown in FIGS. 3A, 3B, and 4, the design of detector 20 packages only those components essential to obtaining the image signal within cassette housing 18. Other components that provide power and control and data communications functions are packaged in electronics housing 40, so that they do not obstruct free-field area 12.

It is instructive to note that the signal levels generated within detection array 26 are relatively weak. Thus, to accurately obtain the signal level for each pixel and minimize the impact of noise, it is most beneficial to position column readout circuitry 28 and row control circuitry 30 as closely as possible to its corresponding sensor element. Components that obtain and buffer these signals should be placed nearby in order to minimize the negative impact of noise and electromagnetic interference (EMI). However, a short separation distance is acceptable, following conventional signal routing practices. Still other supporting components, such as power supply and control and data interface components, can be spaced even further apart from the pixel sensing elements of detection array 26 without perceptible impact on detector performance. Thus, the tethered arrangement of FIG. 4 can provide a useful alternative for component placement for this device.

Figure 5:
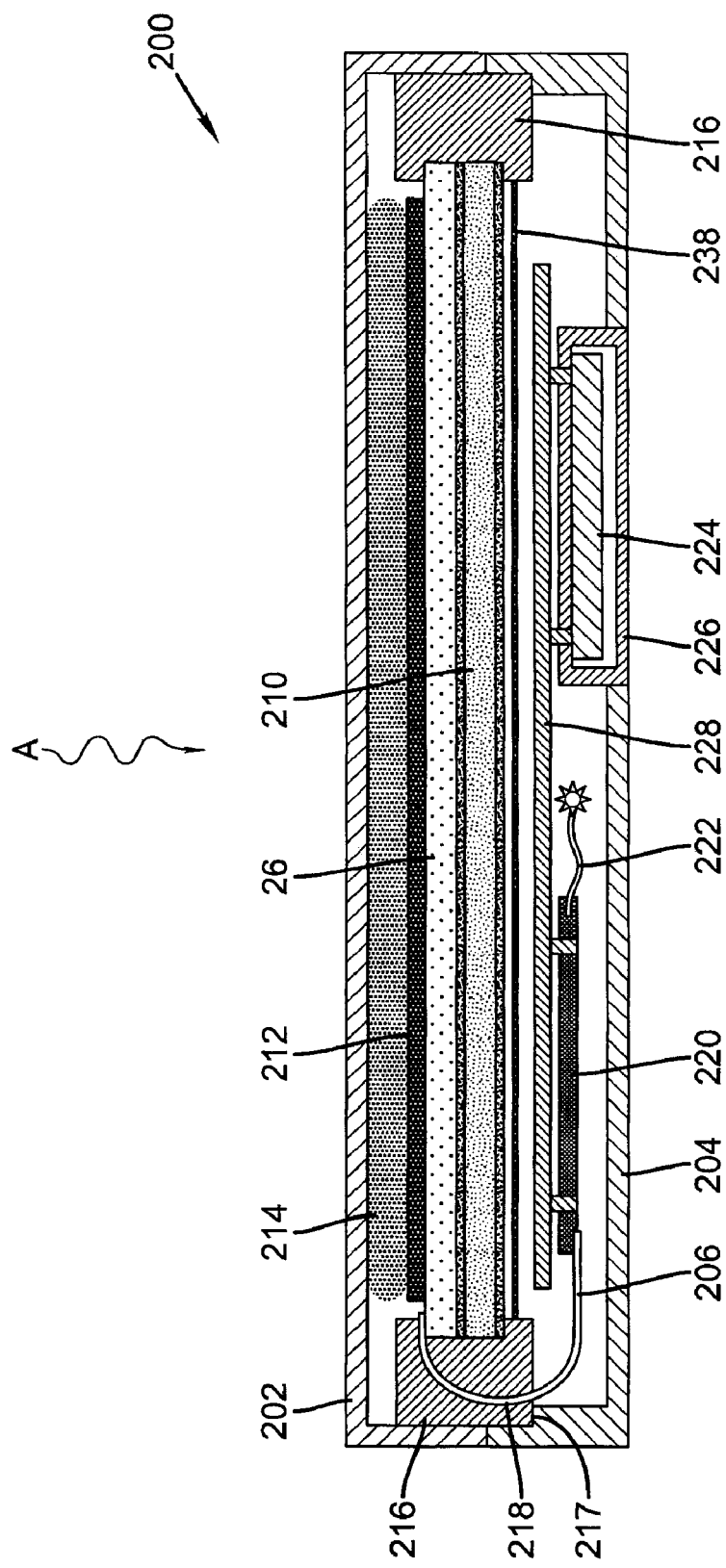
FIG. 5 is a cross-sectional view of a digital mammography detector according to one embodiment.
Figure 6:
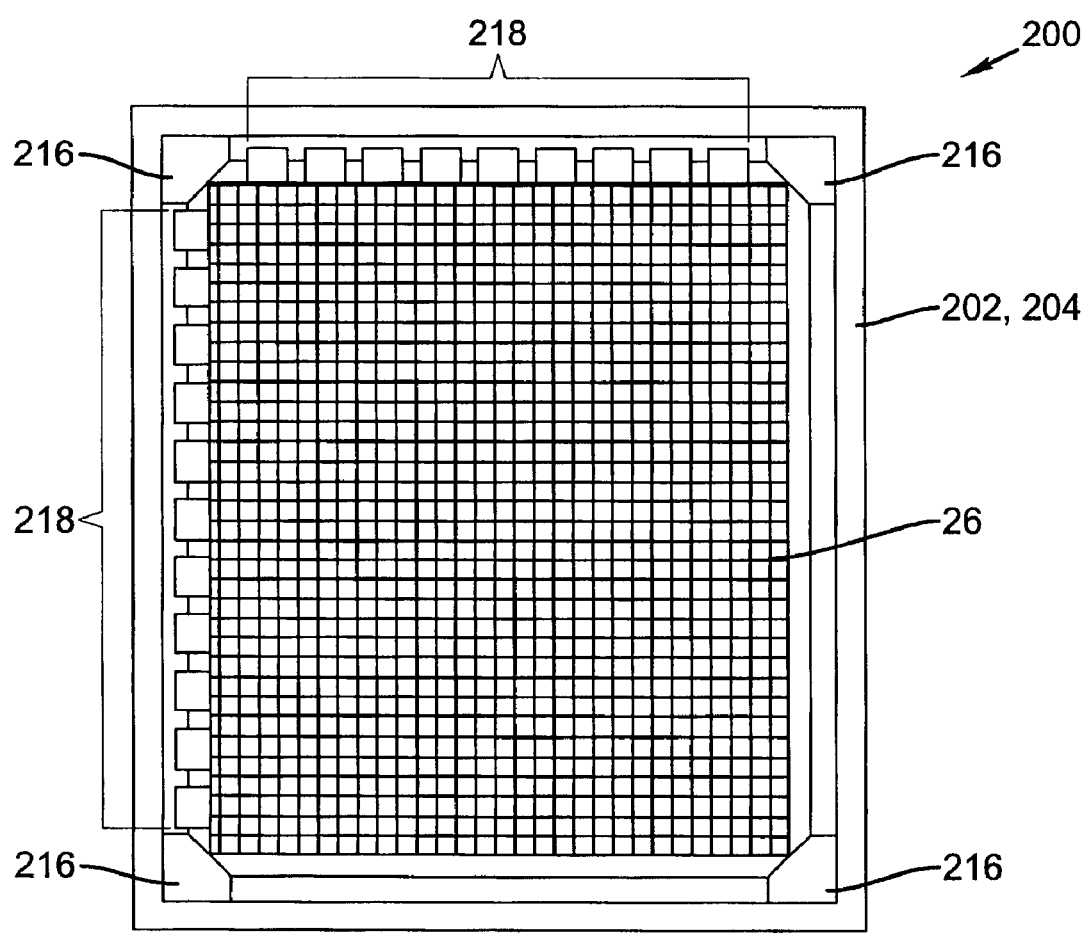
FIG. 6 is a plan view of a digital mammography detector showing the detection array.

An alternate embodiment of the present invention is shown in FIGS. 5 and 6 as disclosed in U.S. patent application Ser. No. 11/441,584 cited earlier. Here, a DR detector 200 includes an upper housing 202 and a lower housing 204, secured together and forming a cavity 206. Mounted within cavity 206 are a detection array 26 mounted on a stiffener 210, a screen (scintillator) 212, a compliant foam member 214, and elastomer shock-absorbing supports 216 mounted on stop ledges 217 of lower housing 204. Flex circuits 218 are connected between detection array 26 and electronics 220. An optional wireless interface 222 is connected to electronics 220. An optional battery pack 224 may be mounted in a compartment 226 of lower housing 204. Battery pack 224 and electronics 220 are thermally coupled to a sheet metal member 228 which acts as a heat sink for heat generated by battery pack 224 and electronics 220. X-rays 106 are projected to DR detector 200 in the direction of arrow A. A shield 238 is provided to protect electronics 220, battery pack 224, and other components.

The embodiment of FIGS. 5 and 6 has the scintillator screen 212 placed in contact with detection array 26 by means of compliant foam member 214 that applies and maintains this physical contact. Physical contact between screen 212 and detection array 26 can alternately be applied by means such as a spring or a plurality of springs. Further, an index-matching type optical adhesive could be used to bond screen 212 directly to detection array 26, so that a compliant foam member is not needed. It is important that physical contact be maintained across the entire active area of the detection array 26 to maximize optical coupling so that uniform and efficient transfer of the converted visible light is achieved.

In order to serve as a retrofit, DR detector 200 is designed for compatibility with the form factor of existing mammography film cassettes. As noted earlier, standard image area dimensions for these film cassettes are 18 cm×24 cm and 24 cm×30 cm, for example, although other sizes may be used. One goal of the design for DR detector 200 is to allow the continued use of automatic exposure control (AEC) components that have been conventionally provided with film-based X-ray imaging systems. However, unlike film, which presents a uniform low attenuation to radiation for auto exposure control sensor 114', DR detector 200 components include solid-state devices formed from crystalline silicon, interconnecting traces, and battery or other power supply components. Further complications result from the need for radiation shielding of at least some portion of these electronic components for DR detector 200. Additionally, the substrate on which detection array 26 is deposited must provide low attenuation to radiation within the free-field area 12, so as to provide sufficient signal to AEC sensor 114'. Thus, the task of providing a DR detector retrofit for an existing film-based X-ray imaging apparatus and retaining AEC capability at the same time presents a considerable challenge.

In one embodiment, DR detector 200 of the present invention addresses this problem by using an alternative arrangement of its internal electronics components. To avoid obstructing free-field area 12, the method of the present invention shifts the position of electronic components and their associated shielding away from this area, to other positions. In addition, because of the need to obtain relatively low-level signals with minimum noise, this rearrangement positions circuitry that is needed in order to capture these signals as closely as possible to their corresponding sensor components, but outside free-field area 12 in as much as is possible.

Figure 7:
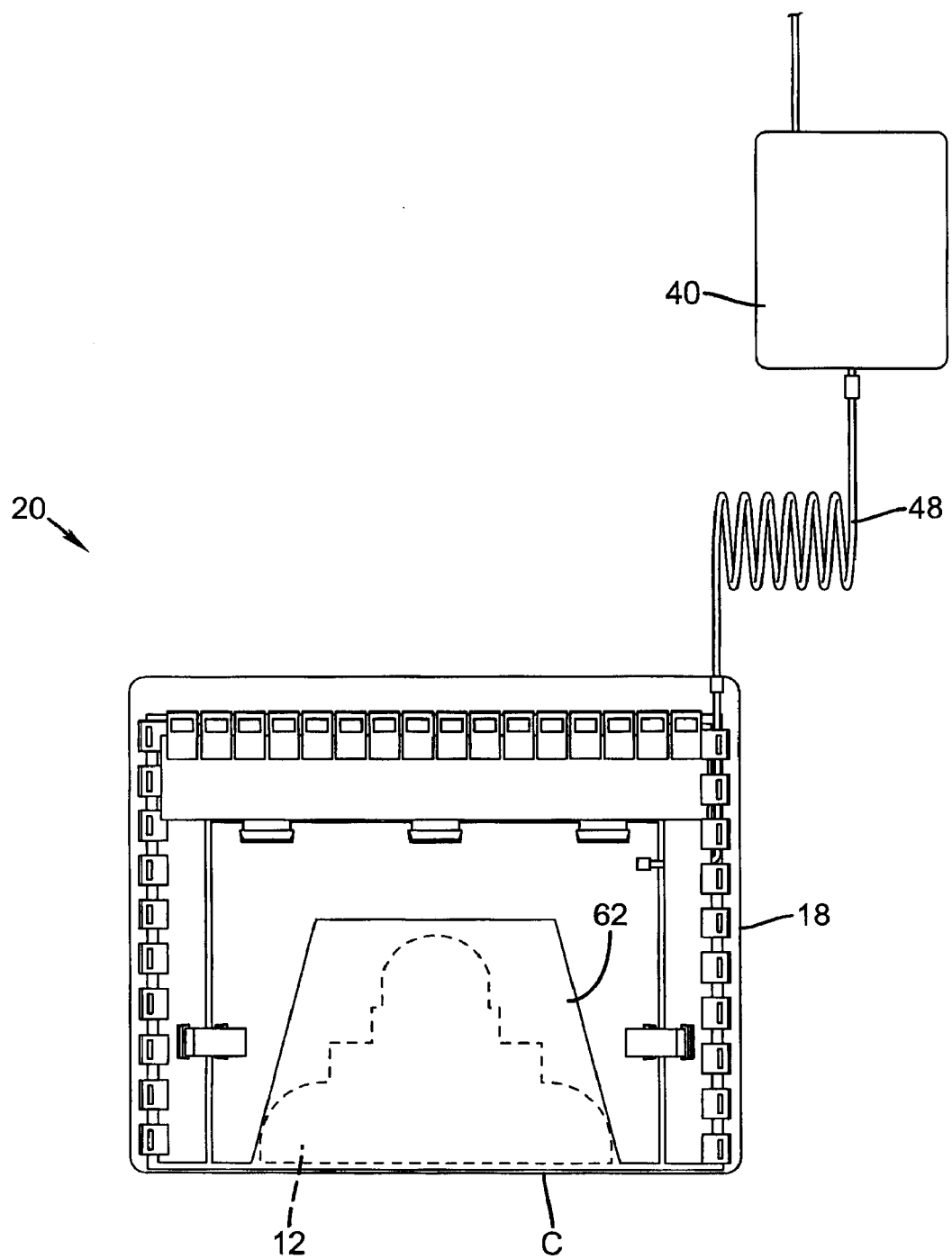
FIG. 7 is a plan view of the tethered DR detector, shown from the side opposite the X-ray tube.

FIG. 7 shows, from a plan view, how a tethered embodiment of detector 20 is arranged. Here, cassette housing 18 (shown from the side opposite the X-ray source and without its cover) contains the essential electronics for obtaining sensed image data, as described earlier with reference to the block diagram of FIGS. 3A and 3B. There is an unobstructed area 62, defined by the outline of shield 238, that corresponds with free-field area 12, shown in dashed outline form in FIG. 7. The chest wall edge is designated by C. As was also described earlier with reference to FIGS. 3A and 3B, electronics housing 40 contains components that can be conveniently placed at some removed distance from the circuitry that obtains low-level signals that provide the image data. A wire or wires 48 connect electronics housing 40 to cassette housing 18.

Figure 8:
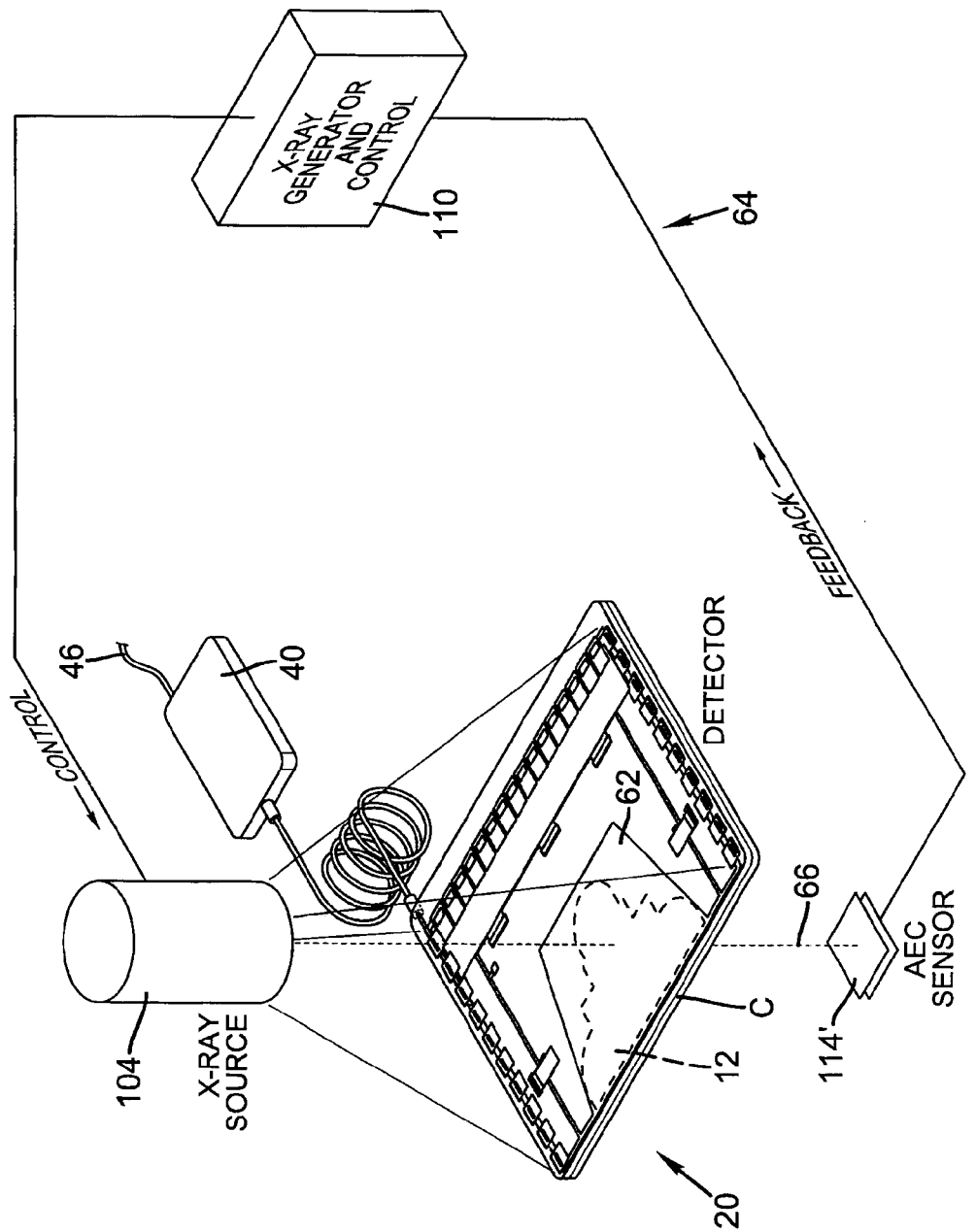
FIG. 8 is a block diagram showing an exposure control loop that uses a tethered DR detector arrangement in one embodiment.

The block diagram of FIG. 8 shows the role of unobstructed area 62 in an AEC control loop 64 when using DR detector assembly 20 of the present invention. For simplicity, the patient is not shown, nor are the downstream image processing components that cooperate to form and display the image data obtained from detector assembly 20. Again, detector assembly 20 is shown without its protective cover and without its scintillator screen 22 (indirect DR) or photoconductor 23 (direct DR). As is represented by a beam 66, a portion of the radiation that transmits through detector assembly 20 is sampled as feedback by AEC sensor 114'. X-ray generator and control 110 then uses this feedback signal to control X-ray source 104, shutting off the radiation when sufficient exposure has been delivered. It is instructive to note that without free-field area 12, control loop 64 with AEC sensor 114' could not be used.

Figure 9:
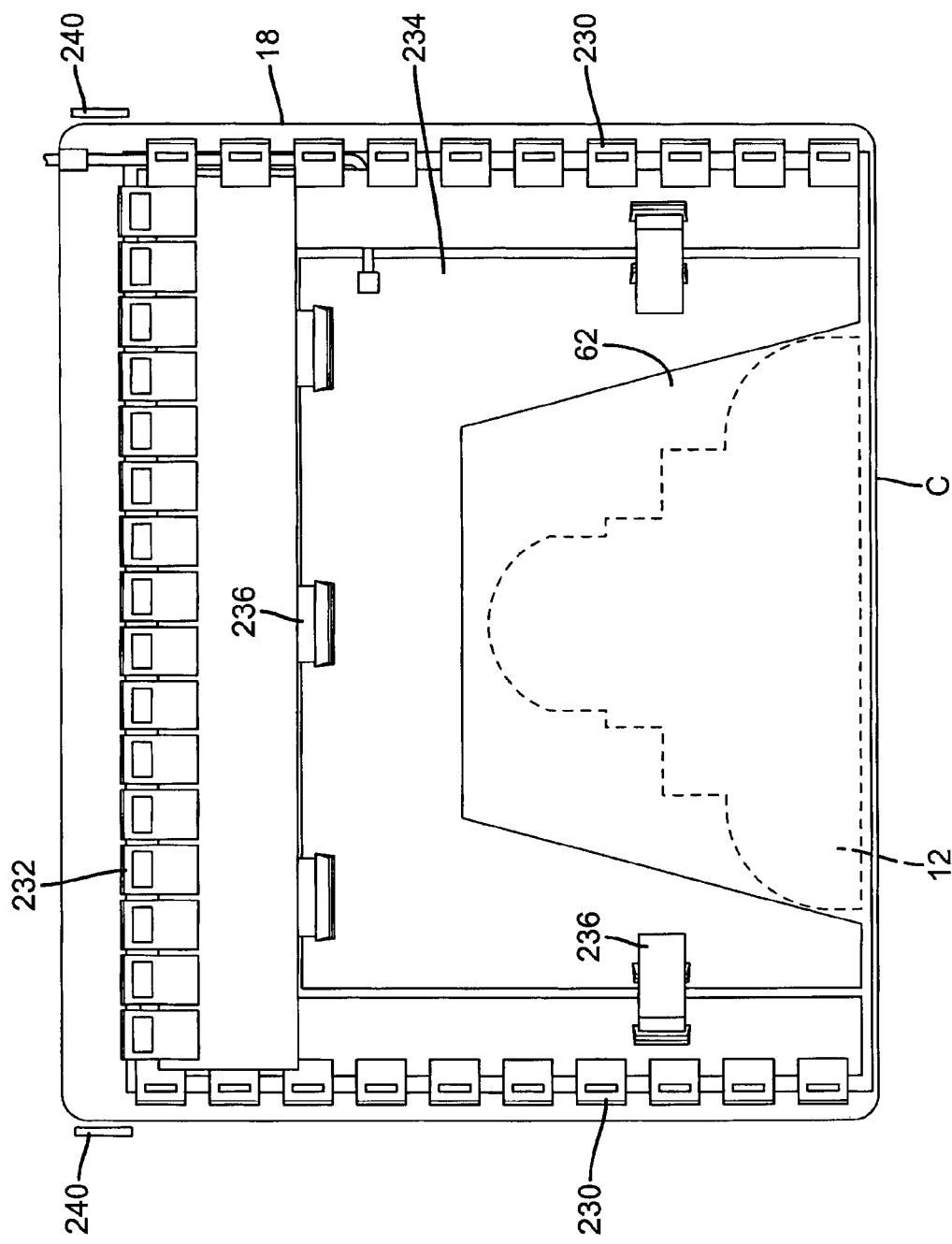
FIG. 9 is a plan view of component layout in the cassette assembly of the DR detector, shown from the side opposite the X-ray tube.

The detailed plan view of FIG. 9 shows the packaging arrangement for electronic components within detector assembly 20 that allows unobstructed area 62 to be reserved for this purpose. Again, free-field area 12 is shown in dashed outline. In order to meet the requirement for compact packaging and chest wall access, this arrangement distributes electronic components that attenuate the X-ray beam away from chest wall edge C and need to be shielded away from unobstructed area 62, so that these components are positioned towards the other edges of cassette housing 18. The outline of shield 238 defines unobstructed area 62. To meet the requirement for highly dense packaging, row driver circuitry 230 is placed along each shorter edge of cassette housing 18. Column readout circuitry 232 is placed along the edge of cassette housing 18 that is opposite the chest wall edge. Readout control and interface circuitry 234 that obtains the low-level signal for each sensed image pixel is positioned nearest to unobstructed area 62. Board interconnects 236 between driver circuitry and readout control and interface circuitry 234 are also placed outside unobstructed area 62. Other interconnecting flexible circuits are also routed so as not to obstruct this region.

The substrate, onto which the detection array 26 is deposited, must be positioned within unobstructed area 62. Typically the detection array is composed of thin-film amorphous silicon components such as transistors and photodetectors having thicknesses in nanometers. These structures are not adversely affected by the X-ray exposure and provide minimal attenuation of the radiation beam.

Substrates used for DR detectors can be made of glass, such as Corning 1737 aluminosilicate glass and Corning EAGLE[2000] fusion-formed glass having a thickness from 0.4 mm to 0.7 mm. In a conventional DR detector, the X-rays from the X-ray beam source (called primary X-rays) are not completely absorbed by the X-ray converter 70. Some X-rays are absorbed by the detection array 26 (i.e., by the signal sensing elements themselves) and some pass through the detection array to encounter the glass substrate that may contain high concentrations of heavy elements such as barium. Some heavy-element atoms, upon absorbing the X-rays, emit lower energy fluorescent X-rays (called secondary X-rays). These secondary X-rays are generated by the absorption of X-rays above the K or L absorption edges of the elements. An electron in the K or L shell is ejected by the absorption of the incident X-ray. When electrons cascade down to fill this vacant lower energy state, X-rays can be produced at energies characteristic for a particular element.

The secondary X-rays can be emitted in any direction, but those emitted back to the phosphor screen can cause a loss of spatial resolution and an increase in image noise resulting in degradation in image quality. To reduce the absorption loss of X-ray radiation through the substrate and the generation of K-fluorescence in the substrate, the thickness of the substrate and the concentration of heavy elements in the substrate should be as small as possible without sacrificing the functionality, mechanical strength, and durability of the substrate. Generally, the absorption loss of X-ray radiation due to the substrate should be less than about 40%, and preferably can be less than about 26% at an X-ray energy of about 28 keV.

Other types of organic and inorganic materials that can be used as substrates for DR detectors include plastics (e.g., polyethylene terephthalate (PET)), polyethylene naphthalate, cellulose acetate, or any other suitable plastic material or combinations thereof), metal foils (e.g., stainless steel, carbon steel, aluminum, anodized aluminum, copper, brass, any other suitable metal, or combinations thereof), or other suitable materials. Generally, PET has been used as the substrate for the phosphor screen and as the emulsion film base in conventional screen-film radiographic apparatus. This material possesses many excellent basic properties such as high mechanical strength, good chemical resistance, low water absorption, and high dimensional stability. Furthermore, it is lighter and sturdier than glass. Moreover, the surface of the PET film can be pretreated during manufacturing to give other desirable surface properties, such as adhesion to evaporated metals and a range of solvent and aqueous-based lacquers, ultraviolet-cured polymers, and photographic gelatins, for which surface energies in excess of 72 dynes/cm can be provided to form strong bonding. The insulating properties of PET film result in high surface resistivities in excess of $10^{14}$ ohm/$m^2$ at 23° C. and 70% relative humidity. More importantly, the PET film is highly permeable to X-rays and produces negligible K-fluorescence X-rays. As a result, the losses of X-ray absorption and spatial resolution caused by the PET substrate are significantly lower than with the glass substrate.

Typically, the DR detector is packaged in a cassette housing having a front panel (facing the incoming X-ray radiation) and a back panel. The panels can be made of X-ray transmissive materials (such as carbon fiber, plastics, and aluminum) to maximize signal detection and to provide adequate radiation for the AEC sensor. The ISO 4090:2001 specification requires that a certain minimum dose must be available to the AEC sensor (about 0.58 mR to 1.14 mR or 5 to 10 μGy) to enable AEC operation.

The table in FIG. 11 shows X-ray transmission through the cassette containing three different DR detectors with various substrate materials and thicknesses and the resulting X-ray exposure available at the AEC sensor. Here, a typical X-ray beam for mammography is used (28 kVp, Mo/Mo, and 4.5 cm Lucite, having a HVL of 0.636 mm Al). The transmission loss through the front and back panels of a typical cassette is about 20%. The three DR detectors considered here are:

Indirect DR detector with a $Gd_2O_2S$:Tb screen (Kodak Min-R phosphor) of 84 um thick, Indirect DR detector with a CsI:T1 screen of 150 um thick, and Direct DR detector with an a-Se layer of 75 um thick.

The X-ray exposure incident on the front panel of the cassette is assumed to be 12 mR, corresponding to a 3 mGy mean glandular dose (MGD) at a typical breast. The X-ray transmission through the $Gd_2O_2S$, CsI, and a-Se detectors are 71.2%, 82.6%, and 81.4%, respectively. It is shown in FIG. 11 that for all cases the X-ray exposure available at the AEC sensor meets the aforementioned ISO requirements.

Figure 10:
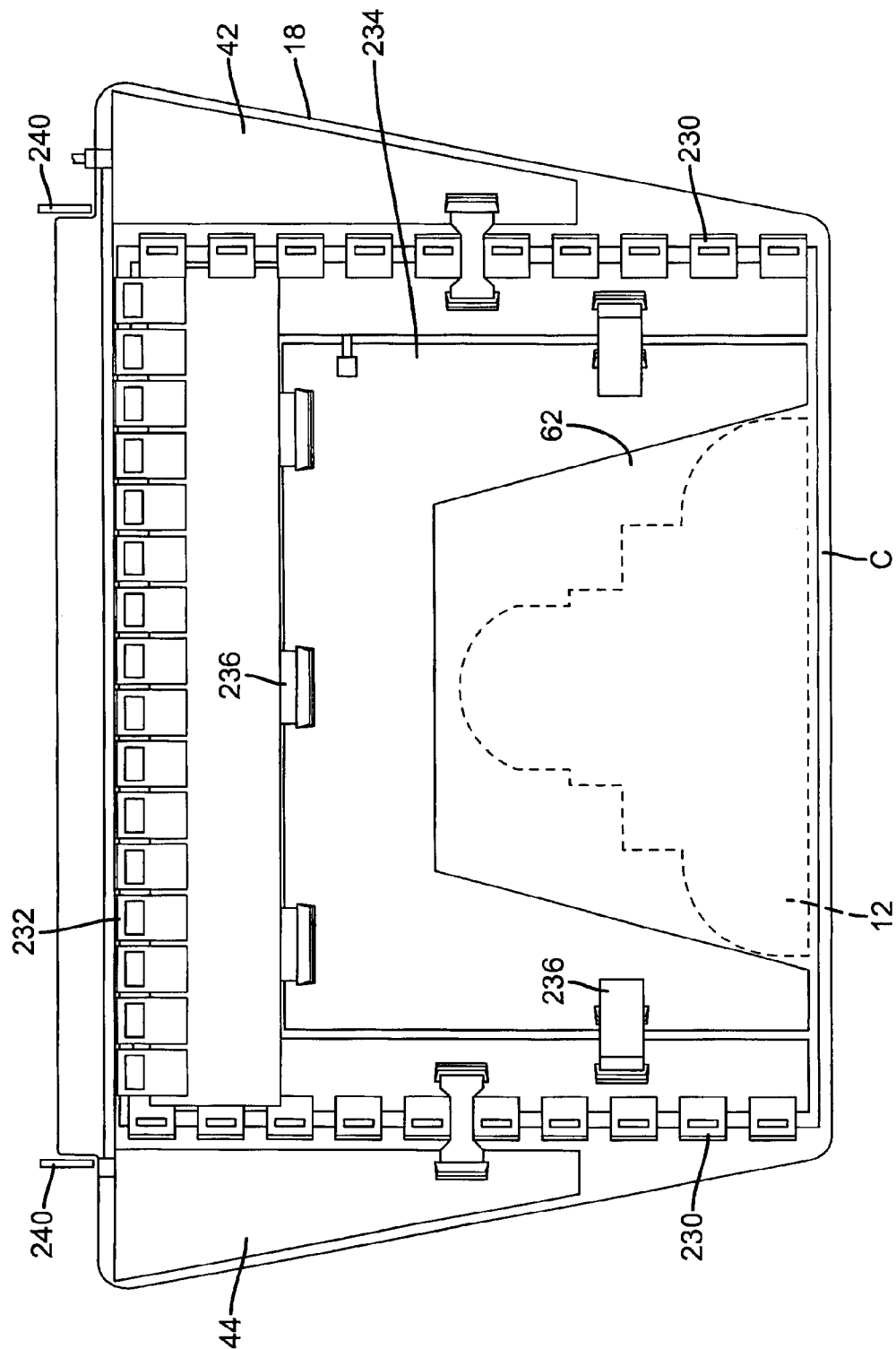
FIG. 10 is a plan view of component layout for a second embodiment with attached electronics assembly, shown from the side opposite the X-ray tube.

It is instructive to emphasize that the arrangement shown in FIG. 9 is one embodiment; many alternate arrangements are possible, provided that unobstructed area 62 be at least substantially free of types of electronic components, such as integrated circuits formed from crystalline silicon, and from shielding that contributes to X-ray signal attenuation and provided that chest wall access requirements be met. For example, detector assembly 20 may include all necessary power, control switching, and signal processing circuitry within cassette housing 18, thus not requiring a tethered arrangement. FIG. 10 illustrates one such embodiment in which power supply 42 and sequencing control 44 components are positioned within a portion of cassette housing 18, in the enclosure adjacent to the detection module. In this embodiment, cassette housing 18 with the added enclosure portion meets the thickness and width specifications for traditional cassettes, but takes advantage of additional available space in the length dimension that does not significantly interfere with patient positioning for mammographic imaging. This space is available in the portion of the X-ray bucky tray that normally is reserved for inserting and removing the film cassette before and after exposure to X-rays. A recessed area is provided in the cassette holding-latch interface location 240 that enables this larger cassette housing 18 to be compatible with equipment that was designed to position and retain standard cassette sizes. Alternately, power source and control electronics may be provided using a suitably configured computer workstation or dedicated logic processor, eliminating the need for electronics housing 40.

It is instructive to note that the conventional DR detector device used for general radiography does not provide the equivalent of unobstructed area 62 as described with respect to FIGS. 7, 8, 9, and 10. Instead of permitting substantially unobstructed transmission of X-rays through a predefined portion of the detector, as in the present invention, the conventional DR detector device blocks X-ray transmission, shielding any electronic components that are positioned behind the scintillator and detector layers. Conventional DR detectors can use existing AEC mechanisms in many cases, where AEC sensor 114 is placed in front of the DR detector to sample X-ray exposure, as was described with reference to FIG. 1. However, the X-ray energy utilized for mammography and the positional placement constraints for its AEC sensor necessitate a change in DR detector design approach for this type of imaging, as shown in the apparatus of the present invention.

In practice, unobstructed area 62 should provide minimal attenuation to the incident X-ray beam. The ISO 4090:2001 specification cited earlier stipulates that a minimum exposure of 0.58-1.14 mR (5-10 µGy) reach the AEC sensor. In order to obtain this minimum exposure level at the AEC sensor, substrate materials used in the detector should not absorb greater than 60% of the X-rays for a typical mammographic X-ray spectrum generated with a peak kilovoltage ranged from 25 to 35 kVp. As shown in FIG. 11, the use of a suitable substrate, such as PET or glass, can be significant for obtaining this performance level. Overall absorption by radiography cassette 108 over free field area 12 should not exceed 95%, preferably not exceeding 90%. The ISO 4090:2001 specification cited earlier also specifies a measure of uniformity in radiation transmission through free-field area 12. Currently, this uniformity value is not more than 5% difference in radiation transmission between any two points in the free-field area that are within a 3.5 cm diameter.

Scintillator Design

In order to provide the needed sensitivity and resolution for mammography, a suitable phosphor material must be used. In one embodiment, cesium iodide (CsI:Tl) is used. In another embodiment, gadolinium oxysulfide ($Gd_2O_2S$:Tb) is used. Other materials can alternately be used. Phosphor material can be directly deposited on the detection array.

Beam Triggered Readout For retrofit application, it is desirable to capture the image at the appropriate time in the exposure cycle without the need to electrically connect with the existing X-ray control system. A "beam triggered readout" is a passive detection/control system that serves this need as disclosed in U.S. patent application Ser. No. 11/409,883 cited earlier. Using this beam-detection feature with the AEC-compatible concept of the present invention, a mammography detector can be retrofit onto an existing mammography exposure system without requiring any modification to the system's electrical circuitry.

The invention has been described in detail with particular reference to certain preferred embodiments thereof, but it will be understood that variations and modifications can be effected within the scope of the invention. For example, power for detector 20 components can be supplied by batteries installed within cassette housing 18 or externally, from a conventional dc power source. Detector 20 could alternately be a direct DR system, not using a scintillator and detector, but providing the radiation-to-signal conversion through the use of a photoconductor such as amorphous selenium and a thin-film-transistor array with pixel charge plates.

Thus, what is provided is a digital radiography detector that can be retrofit into an existing film-based mammography exposure system.

PARTS LIST 10 detector
12 free-field area
18 cassette housing
20 detector assembly
22 scintillator screen
23 photoconductor
24 detection module
26 detection array
28 column readout circuitry
30 row control circuitry
32 readout control circuitry
40 electronics housing
42 power supply
44 sequencing control
46 antenna
48 wire
50 computer
52 control logic processor
54 high speed interface
56 image handling subsystem
60 radiographic system
62 unobstructed area
64 control loop
66 X-ray beam
70 X-ray converter
74 Readout electronics
100 patient
102 support
104 X-ray source
106 X-rays
108 radiography cassette
110 X-ray generator and control
112 antiscatter grid
114 auto exposure control sensor
114' auto exposure control sensor
116 detector control
118 host computer
200 DR detector
202 upper housing
204 lower housing
206 cavity
210 stiffener
212 scintillator screen
214 compliant foam member
216 elastomer supports
217 stop ledges
218 flex circuits 220 electronics
222 wireless interface
224 battery pack
226 compartment
228 sheet metal member
230 row driver circuitry
232 column readout circuitry
234 readout control and interface circuitry
236 interconnect
238 shield
240 cassette holding-latch interface location

The invention claimed is:

1. A digital radiography detector comprising:
 a) a first housing, having substantially a form factor of a film cassette and having a chest wall edge, the first housing comprising:
  (i) an X-ray converter coupled with a detection array, wherein each detector in the detection array generates a signal according to an amount of radiation received;
  (ii) readout electronics coupled with switching elements in the detection array for obtaining the signals therefrom, wherein the readout electronics comprise elements formed from crystalline silicon and wherein the readout electronics are distributed toward outer edges of the first housing and away from the chest wall edge of the first housing;
  (iii) X-ray shielding selectively protecting the readout electronics and located beneath a portion of the X-ray converter, the shielding defining an area permitting passage of radiation beyond the housing; and
 b) a second housing electrically connected to the first housing and comprising:
  (i) a power source for the detection and switching element arrays; and
  (ii) control electronics for obtaining signals provided from the readout electronics in the first housing.

2. The digital radiography detector of claim 1 wherein the second housing further comprises wireless transmission components.

3. The digital radiography detector of claim 1 wherein the detection array is formed on a glass substrate.

4. The digital radiography detector of claim 1 wherein the detection array is formed on a plastic substrate.

5. The digital radiography detector of claim 1 wherein the detection array is formed on a flexible substrate.

6. The digital radiography detector of claim 1 wherein the first housing has an unshielded portion that corresponds to a free-field area for automatic exposure control.

7. The digital radiography detector of claim 1 wherein the X-ray converter comprises a scintillator screen optically coupled with the detection array, wherein the detection array comprises a plurality of light sensors, and wherein each light sensor generates a signal according to an amount of light received.

8. The digital radiography detector of claim 1 wherein the X-ray converter comprises a photoconductor electrically coupled to the detection array, wherein the detection array comprises a plurality of detectors, and wherein each detector generates a signal according to an amount of X-ray radiation received.

9. The digital radiography detector of claim 1 wherein, over the area not protected by the X-ray shielding, for X-ray spectra generated with a peak kilovoltage ranged from 25 to 35 kVp, absorption of X-rays does not exceed 90%.

10. The digital radiography detector of claim 1 wherein the substrate on which the detection array is deposited does not absorb more than 60% of X-rays for X-ray spectra generated with a peak kilovoltage ranged from 25 to 35 kVp.

11. The digital radiography detector of claim 1, wherein the area is substantially unobstructed by the readout electronics.

12. The digital radiography detector of claim 1, wherein the radiation passing through the area contacts an automatic exposure control sensor disposed outside of the first and second housings.

13. A digital radiography detector comprising:
 a) a first housing comprising:
  (i) a scintillator screen that emits light proportional to received X-ray radiation;
  (ii) a detection array optically coupled with the scintillator screen, wherein the detection array comprises a plurality of light sensors wherein each light sensor generates a signal according to an amount of light received;
  (iii) readout electronics coupled with the plurality of light sensors through switching elements in the detection array for obtaining the signals therefrom, wherein the readout electronics comprises elements formed from crystalline silicon;
  (iv) X-ray shielding selectively protecting the readout electronics and located beneath a portion of the scintillator and detection array, the shielding defining an area permitting passage of radiation beyond the housing;
 wherein the first housing has substantially a form factor of a film cassette and has a chest wall edge, and wherein the readout electronics are distributed toward outer edges and away from the chest wall edge of the first housing; and
 b) a second housing electrically connected to the first housing and comprising:
  (i) a power source for the detection and switching element arrays; and
  (ii) control electronics for obtaining signals provided from the readout electronics in the first housing.

14. The digital radiography detector of claim 13 wherein the scintillator screen comprises cesium iodide (CsI:Tl).

15. The digital radiography detector of claim 13 wherein the scintillator screen comprises gadolinium oxysulfide ($Gd_2O_2S$:Tb).

16. A digital radiography detector comprising:
 a) a first housing comprising:
  (i) a photoconductor that generates a charge signal proportional to received X-ray radiation;
  (ii) a detection array comprising a plurality of detectors, wherein each detector provides an output signal proportional to received X-ray radiation and is coupled with a switching element;
  (iii) readout electronics coupled with the plurality of switching elements in the detection array for obtaining the output signals therefrom, wherein the readout electronics comprises elements formed from crystalline silicon;
  (iv) X-ray shielding selectively protecting the readout electronics and located beneath a portion of the detection array, the shielding defining an area permitting passage of radiation beyond the housing;
 wherein the first housing has substantially a form factor of a film cassette and has a chest wall edge, and wherein the readout electronics are distributed toward outer edges and away from the chest wall edge of the first housing; and b) a second housing electrically connected to the first housing and comprising:
  (i) a power source for the detection and switching element arrays; and
  (ii) control electronics for obtaining signals provided from the readout electronics in the first housing.

17. A digital radiography detector for mammography comprising:
  a) a housing having a form factor in conformance with mammography film cassettes;
  b) a two-dimensional detection array coupled with an X-ray converter within the housing, wherein each detection element in the detection array comprises a thin-film component that generates a signal according to received radiation;
  c) system electronics connected to detection elements through switching elements in the detection array and comprising components formed from crystalline silicon; and
  d) X-ray shielding over system electronics elements and defining an area permitting passage of radiation beyond the housing, wherein the area is substantially unobstructed by system electronics components, allowing a portion of radiation to be obtained by an automatic exposure control sensor.

18. A digital radiography detector comprising
  a) a housing, having substantially a form factor of a film cassette and having a chest wall edge;
  b) an X-ray converter within the housing, coupled with a detection array, wherein each detection element in the detection array generates a signal according to an amount of radiation received;
  c) readout electronics coupled with detection elements through switching elements in the detection array for obtaining the signals therefrom, wherein the readout electronics comprise elements formed from crystalline silicon and wherein the readout electronics are distributed peripherally with respect to an imageable area and away from a chest wall edge of the housing; and
  d) X-ray shielding selectively protecting the readout electronics, the shielding defining an area permitting passage of radiation beyond the housing for automatic exposure control sensing.

19. The digital radiography detector of claim 18 wherein the housing has substantially the form factor of a film cassette in two dimensions and contains extensions in the third dimension that enable acceptable positioning of said detector near the patient while providing additional space for electronics and compatibility with cassette holding features of existing X-ray exposure equipment.

20. A radiography imaging system comprising:
  a) an X-ray source;
  b) an exposure control apparatus comprising a sensor in the path of radiation from the X-ray source and an X-ray control; and
  c) a digital radiography detector interposed between the X-ray source and the sensor of the exposure control apparatus, wherein the digital radiography detector comprises:
    (i) a first housing comprising an X-ray converter, the X-ray converter coupled with a detection array, wherein each detector in the detection array generates a pixel signal according to an amount of radiation received and is coupled with a switching element;
    (ii) readout electronics in the first housing and coupled with switching elements in the detection array for obtaining the pixel signals therefrom, wherein the readout electronics comprise elements formed from crystalline silicon and wherein the readout electronics are distributed toward outer edges of the first housing and away from a chest wall edge of the first housing;
    (iii) X-ray shielding selectively protecting the readout electronics and located beneath a portion of the X-ray converter, the shielding defining an area permitting passage of radiation beyond the housing; and
    (iv) a second housing electrically connected to the first housing and comprising a power source for the detection and switching element arrays and control electronics for obtaining signals provided from the readout electronics in the first housing.

* * * * *